United States Patent [19]

Treiber et al.

[11] Patent Number: 5,538,972
[45] Date of Patent: Jul. 23, 1996

[54] IMIDAZOLOQUINOXALINONES FOR THE TREATMENT OF CENTRAL NERVOUS DISORDERS

[75] Inventors: Hans-Joerg Treiber, Bruehl; Berthold Behl; Hans P. Hofmann, both of Limburgerhof, all of Germany

[73] Assignee: BASF Aktiengesellschaft, Ludwigshafen, Germany

[21] Appl. No.: 525,550

[22] PCT Filed: Mar. 19, 1994

[86] PCT No.: PCT/EP94/00872

§ 371 Date: Sep. 19, 1995

§ 102(e) Date: Sep. 19, 1995

[87] PCT Pub. No.: WO94/22447

PCT Pub. Date: Oct. 13, 1994

[30] Foreign Application Priority Data

Mar. 31, 1993 [DE] Germany .......................... 43 10 523.8

[51] Int. Cl.$^6$ ........................................ A61K 31/495
[52] U.S. Cl. ........................................ 514/250
[58] Field of Search ................................ 514/250

[56] References Cited

U.S. PATENT DOCUMENTS 4,291,033  9/1981  Barnes et al. .
5,153,196  10/1992  McQuaid et al. .
5,166,344  11/1992  Davey .
5,182,386  1/1993  Albaugh et al. .

FOREIGN PATENT DOCUMENTS 400583  12/1990  European Pat. Off. .
518530  12/1992  European Pat. Off. .
3004750  8/1980  Germany .
3004751  8/1980  Germany .

*Primary Examiner*—Raymond Henley, III
*Attorney, Agent, or Firm*—Keil & Weinkauf

[57] ABSTRACT

The use of imidazoloquinoxalinones for the production of drugs for controlling central nervous disorders is described. The imidazoloquinoxalinones have the formula

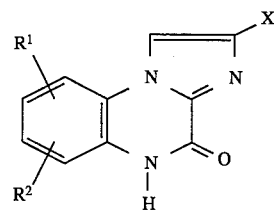

in which $R^1$, $R^2$ and X have the meanings indicated in the description.

2 Claims, No Drawings

IMIDAZOLOQUINOXALINONES FOR THE TREATMENT OF CENTRAL NERVOUS DISORDERS

This application is a 371 of PCT/EP94/00872 filed Mar. 13, 1994.

The present invention relates to the use of imidazoloquinoxalinones for the treatment of central nervous disorders.

Imidazoloquinoxalinones of the formula I have been disclosed in DE-A 30 04 750 and DE-A 30 04 751. An antiallergic action is reported for these compounds.

It is furthermore known that certain imidazoloquinoxalinones disclosed in EP-A 518 530 ($\hat{=}$ U.S. Pat. No. 5,153,196) have an antagonistic effect on the receptors of amino acids with excitatory activity. They are therefore suitable as neuroprotective agents and for eliminating neurological disturbances associated with this mechanism of action. Furthermore, a number of imidazoloquinoxalinones substituted in different ways have been disclosed as cAMP phosphodiesterase inhibitors with an effect on the circulation (EP-A 400 583 $\hat{=}$ U.S. Pat. No. 5,166,344) and as GABA receptor ligands for the treatment of various disturbances of the central nervous system (U.S. Pat. No. 5,182,386).

The present invention relates to the use of compounds of the formula I

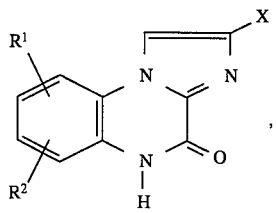

where

X is a carboxyl group which can be in the form of its salt with a physiologically tolerated amine cation or metal cation; the radical

where $R^3$ is $C_{1-8}$-alkyl or benzyl; or X is a hydroxymethyl, cyano, formyl, tetrazolyl, carbonylaminotetrazole, carbamoyl, oxime or $C_1$–$C_3$-alkoxime ether group and $R^1$ and $R^2$ are identical and are hydrogen, chlorine or bromine atoms, for the production of drugs for the treatment of disorders of the central nervous system.

Examples of relevant disorders of the central nervous system are epilepsy, brain damage, Parkinson's disease, Alzheimer's disease, emesis, and trauma of the head and spinal cord. The effect of the compounds derives from their glutamate-antagonistic properties.

The novel pharmacological activity of the compounds I was investigated on isolated membrane material from rat cerebra. To do this, the membrane material was treated in the presence of the compounds with the radiolabeled substances $^3$H-2-amino-3-hydroxy-5-methyl-4-isoxazolepropionic acid ($^3$H-AMPA) and $^3$H-5,7-dichlorokynurenic acid, these binding to specific receptors (AMPA and NMDA (N-methyl-D-aspartate) receptors respectively). The radioactivity in the treated membranes was subsequently measured by scintillation counting. The amounts of bound $^3$H-AMPA and $^3$H-5,7-dichlorokynurenic acid were calculated from the bound radioactivity. The active substance according to the invention was determined by iterative non-linear regression analysis using the statistical analysis system (SAS) on an IBM computer, similar to the "Ligand" program of P. J. Munson and D. Rodbard (Analytical Biochem. 107 (1980) 220, Ligand: Versatile Computerized Approach for Characterization of Ligand Binding Systems).

The following in vitro investigations were carried out:

1. Binding of $^3$H-2-amino-3-hydroxy-5-methyl-4-isoxazolpropionic acid ($^3$H-AMPA)

To prepare the membrane material, freshly removed rat cerebra were homogenized together with 15 times the volume of a buffer solution A consisting of 30 mM $\alpha$, $\alpha$, $\alpha$-tris(hydroxymethyl)methylamine hydrochloride (TRIS-HCl) and 0.5 mM ethylenediaminetetraacetic acid (EDTA), pH 7.4, using an Ultra-TURRAX. The suspension was centrifuged at 48,000 g for 20 minutes. After removal of the supernatant liquid, the protein-containing membrane material present in the sediment was washed three times by suspension in buffer solution A and subsequent centrifugation at 48,000 g for 20 minutes each time. The membrane material was then suspended in 15 times the volume of buffer solution A and incubated at 37° C. for 30 minutes. Subsequently, the protein material was washed twice by centrifugation and suspension and stored at −70° C. until used.

For the binding assay, the protein material was thawed at 37° C. and washed twice by centrifugation at 48,000 g (20 minutes) and subsequent suspension in a buffer solution B consisting of 50 mM TRIS-HCl, 0.1M potassium thiocyanate and 2.5 mM calcium chloride, pH 7.1. Subsequently, 0.25 mg of membrane material, 0.1 µCi of $^3$H-AMPA (60 Ci/mmol) and compound I were dissolved in 1 ml of buffer solution B and incubated on ice for 60 minutes. The incubated solution was filtered through a CF/B filter (from Whatman) which had previously been treated with a 0.5% strength aqueous solution of polyethyleneimine for at least 2 hours. The filter was then washed with 5 ml of cold buffer solution B in order to separate bound and free 3H-AMPA from one another. After measurement of the radioactivity of the bound $^3$H-AMPA in the membrane material by scintillation counting, the $K_I$ was determined by regression analysis of the displacement plots.

2. 3H-glycine binding assay

Freshly removed rat hippocampi are homogenized in 10 times the volume of preparation buffer (50 mMTris-HCl, 10 mM EDTA) using a Potter homogenizer. The homogenate is centrifuged at 48,000×g for 20 minutes. The supernatant is discarded, and the membranes present in the pellet are washed 2×by resuspension and centrifugation at 48,000×g (20 minutes each time). The resuspended membranes are frozen in liquid nitrogen and thawed again at 37° C. After another washing step, the membrane suspension is incubated in a shaking waterbath at 37° C. for 15 minutes. After a further 4 washing steps (centrifugation at 48,000×g for 20 minutes and resuspension in preparation buffer each time), the membranes are stored at −70° C. until used further.

The frozen membranes are thawed at 37° C. and washed 2×by centrifugation at 48,000×g (20 minutes) and subsequent resuspension in binding buffer (50 mM Tris-HCl pH 7,4; 10 mM MgCl$_2$). An incubation mixture contains 0.25 mg of protein (membranes), 25 nM $^3$H-glycine (16 Ci/mmol) and the substances to be tested in a total of 0.5 ml of binding buffer. The non-specific binding is determined by adding 1 mM glycine. After incubation at 4° C. for 60 minutes, bound and free ligand are separated from one another by filtration through GF/B filters and subsequent washing with about 5 ml of ice-cold binding buffer. The radioactivity remaining on the filters is determined by liquid scintillation counting. The dissociation constants are calculated from the displacement plots using an iterative non-linear fitting program or in accordance with the Cheng and Prusoff equation.

The following results were obtained in these assays with the compounds of claim 1:

|  | $^3$H-Glycine | $^3$H-AMPA |
| --- | --- | --- |
| Substance of Example 1 | 110 | 250 |
| Substance of Example 1 (Ethyl ester) | 162 | 558 |

The pharmaceutical compositions contain a therapeutically effective amount of compound I in addition to conventional pharmaceutical ancillary substances. They can be administered in various ways, such as orally, parenterally, subcutaneously, intraperitoneally and topically. Thus, possible presentations are tablets, emulsions, infusion and injection solutions, pastes, ointments, gels, creams, lotions, dusting powders and sprays.

For local external use, e.g. in dusting powders and ointments, the active substances can be present therein in the usual concentrations. The amount is, as a rule, from 1 to 50% by weight.

For internal use, the preparations are administered in single doses. From 0.1 to 50 mg, preferably 0.1 to 10 mg, of active substance are given per kg of body weight in a single dose. The compositions can be administered in one or more dosages each day depending on the nature and severity of the disorder. The daily dose is, as a rule, from 0.1 to 10 mg per kg of body weight on oral administration and from 0.01 to 50 mg per kg of body weight on parenteral administration.

Besides the active substance, the pharmaceutical compositions according to the invention contain the conventional carriers and diluents appropriate for the desired mode of administration. It is possible to use for local external administration the ancillary substances used in pharmaceutical technology, such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is furthermore possible for antioxidants such as tocopherol and butylated hydroxyanisole and butylated hydroxytoluene, flavor-improving additives, stabilizers, emulsifiers and lubricants to be present in the administration forms.

The substances present in the composition besides the active substance, and the substances used in producing the pharmaceutical composition, must be toxicologically acceptable and compatible with the particular active substance.

The pharmaceutical compositions are produced in a conventional way.

EXAMPLE 1

Tablets of the following composition are compressed in a tabletting machine in a conventional way:

40 mg of 7,8-dichloro-4,5-dihydro-4-oxo-imidazolo[1,2-a]-quinoxaline-2-carboxylic acid 120 mg of corn starch 13.5 mg of gelatin 45 mg of lactose 2.25 mg of Aerosil® (chemically pure silica in submicroscopically fine dispersion)

6.75 mg of potato starch (as 6% paste)

EXAMPLE 2

Coated tablets of the following composition are produced in a conventional way 20 mg of 7,8-dichloro-4,5-dihydro-4-oxo-imidazolo[1,2-a]-quinoxaline-2-carboxylic acid 60 mg of core composition 60 mg sugar-coating composition The core composition consists of 9 parts of corn starch, 3 parts of lactose and 1 part of Luviskol® VA 64 (60:40 vinylpyrrolidone/ vinyl acetate copolymer, cf. Pharm. Ind. 1962, 586). The sugar-coating composition consists of 5 parts of sucrose, 2 parts of corn starch, 2 parts of calcium carbonate and 1 part of talc.

The coated tablets produced in this way are subsequently provided with an enteric coating.

EXAMPLE 3

10 g of 7,8-dichloro-4,5-dihydro-4-oxo-imidazolo[1,2-a]quin-oxaline-2-carboxylic acid are dissolved in 5000 ml of water with the addition of NaCl and adjusted to pH 6.0 with 0.1N NaOH to result in a solution which is isotonic with blood. 5 ml portions of this solution are introduced into ampoules and sterilized.

We claim:

1. A method of treating disorders of the central nervous system which comprises administering to a patient in need thereof an effective amount of one or more compounds of the formula I

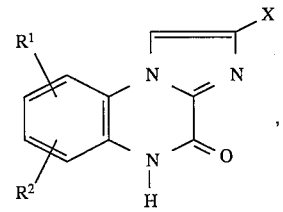

where

X is a carboxyl group which can be in the form of its salt with a physiologically tolerated amine cation or metal cation; the radical

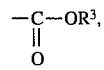

where $R^3$ is $C_{1-8}$-alkyl or benzyl; or X is a hydroxymethyl, cyano, formyl, tetrazolyl, carbonylaminotetrazole, carbamoyl, oxime or $C_1$–$C_3$-alkoxime ether group and $R^1$ and $R^2$ are identical and are hydrogen, chlorine or bromine atoms.

2. A method as defined in claim 1, wherein an effective amount of 7,8-dichloro-4,5-dihydro-4-oxo-imidazolo(1,2-a)-quinoxaline-2-carboxylic acid is administered to the patient.

* * * * *